United States Patent [19]
Rahn et al.

[11] Patent Number: 5,692,515
[45] Date of Patent: Dec. 2, 1997

[54] APPARATUS FOR ACQUIRING STIMULATED ACTION CURRENTS OF THE HEART, FOR BODY SURFACE POTENTIAL MAPPING (BSPM)

[75] Inventors: Norbert Rahn, Erlangen; Wolfgang Eck, Kleinsendelbach, both of Germany

[73] Assignee: Siemens Aktiengesellschaft, Munich, Germany

[21] Appl. No.: 646,391

[22] Filed: May 8, 1996

[30] Foreign Application Priority Data

May 24, 1995 [DE] Germany .................. 195 19 237.0

[51] Int. Cl.$^6$ ............................ A61B 5/04; A61B 5/0402
[52] U.S. Cl. ............................................. 128/710; 128/697
[58] Field of Search ............... 607/9, 10, 5; 128/697, 128/710, 712

[56] References Cited

U.S. PATENT DOCUMENTS

| | | | |
|---|---|---|---|
| 4,674,509 | 6/1987 | De Cote, Jr. | 128/697 |
| 4,741,341 | 5/1988 | Marach | 128/697 |
| 4,919,144 | 4/1990 | Vandehey | 128/705 |
| 4,964,410 | 10/1990 | Leahey et al. | 128/710 |
| 5,161,527 | 11/1992 | Nappholz et al. | 607/4 |
| 5,295,484 | 3/1994 | Marcus et al. | 128/710 |
| 5,311,873 | 5/1994 | Savard et al. | 128/696 |
| 5,330,506 | 7/1994 | Alferness et al. | 607/10 |
| 5,391,187 | 2/1995 | Freeman | 607/5 |
| 5,391,192 | 2/1995 | Lu et al. | 128/697 |
| 5,469,857 | 11/1995 | Laurent et al. | 128/710 |

FOREIGN PATENT DOCUMENTS

| | | | |
|---|---|---|---|
| 0 356 573 | 3/1990 | European Pat. Off. | A61N 1/08 |
| 1 321 552 | 6/1973 | United Kingdom | A61B 5/02 |
| 2 083 915 | 3/1982 | United Kingdom | A61B 5/04 |
| 2 153 084 | 8/1985 | United Kingdom | A61B 5/04 |

OTHER PUBLICATIONS

"Alignment Methods for Averaging of High–Resolution Cardiac Signals: A Comparative Study of Performance," Janéet al, IEEE Trans. on Biomed. Eng., vol. 38, No. 6, Jun. 1991 (pp. 571–579).

"Conductive Cardiograph–Bundle of His Detector," Siegel et al, IEEE Trans. on Biomed. Eng., vol. BME–22, No. 4, Jul. 1975 (pp. 269–273).

"A Microcomputer–Controlled 3–Channel Stimulator for Investigating Atrial and Ventricular Vulnerability of the Heart," Heuer et al. Biomed. Techn., vol. 26, No. 6, 1981 (pp. 130–135).

"Medizinische Elektronik," Eichmeier, 1991 (pp. 162–163).

*Primary Examiner*—William E. Kamm
*Assistant Examiner*—Carl H. Layno
*Attorney, Agent, or Firm*—Hill, Steadman & Simpson

[57] ABSTRACT

In an apparatus for acquiring stimulated action currents of the heart, a stimulation unit emits stimulation signals to the heart. Measured values that are causally influenced by the action currents resulting from the stimulation signals are acquired with a measuring system. The measured values are supplied to a processing unit under the control of a unit connected to the stimulation unit and to the processing unit which supplies the measured values to the processing unit dependent on the stimulation signals.

18 Claims, 1 Drawing Sheet

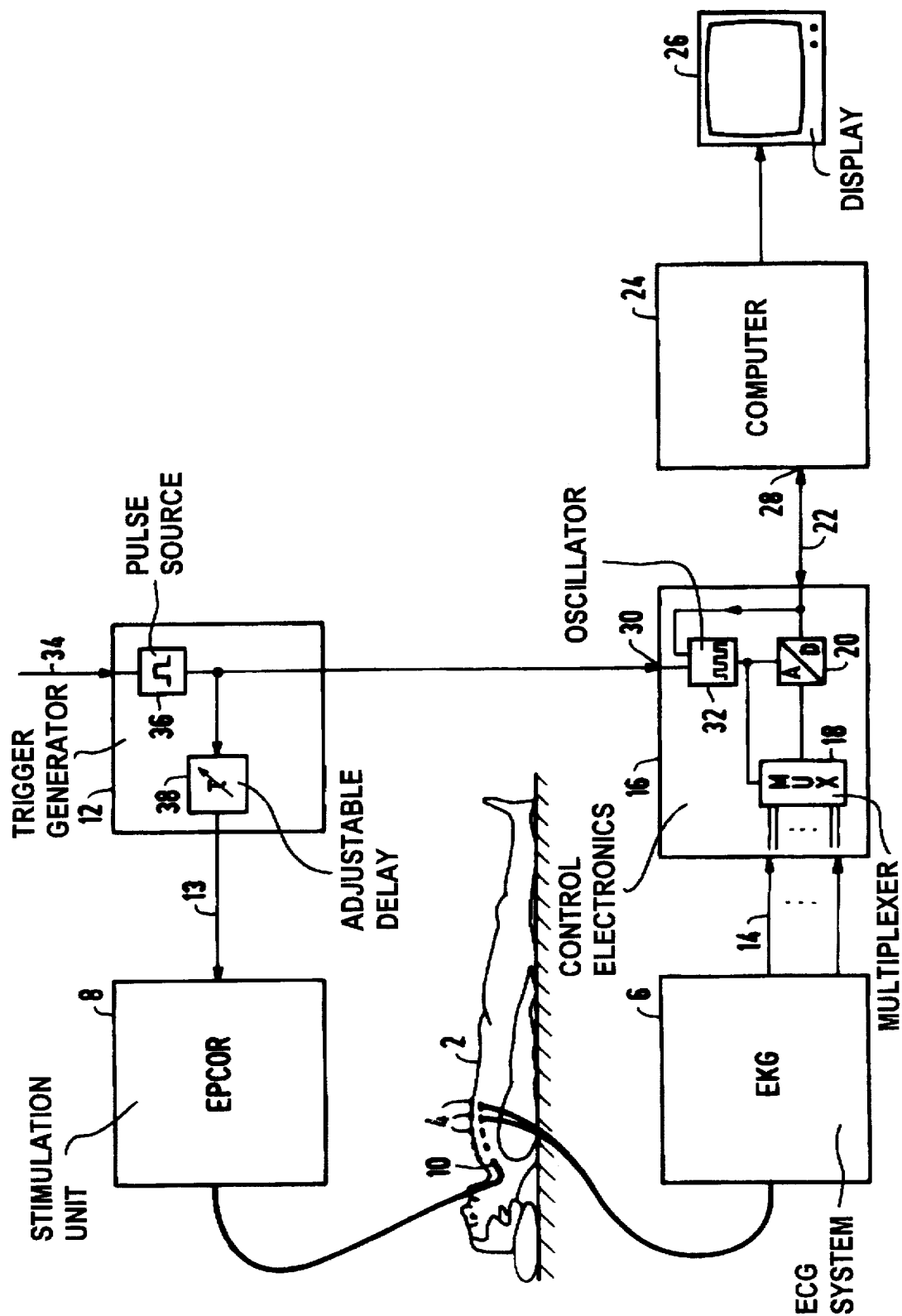

APPARATUS FOR ACQUIRING STIMULATED ACTION CURRENTS OF THE HEART, FOR BODY SURFACE POTENTIAL MAPPING (BSPM)

BACKGROUND OF THE INVENTION

1. Field of the Invention

The present invention is directed to an apparatus for acquiring stimulated action currents of the heart having a stimulation unit that emits stimulation signals to the heart, a measuring system with which measured values are acquired that are representative of the action currents, and a processing unit to which the measured values are supplied.

2. Description of the Prior Art

U.S. Pat. No. 5,311,873 discloses an apparatus of the above general type. The location of the excitation anomalies in the heart is identified by guiding a stimulation catheter connected to the stimulation unit into the proximity of the location of the excitation anomaly in the heart via a vein or an artery. The catheter emits stimulation signals during the positioning of the catheter. At the same time, potentials (ECG signals) generated by the stimulated action currents are measured at the body surface or intracardially as well with a multi-channel electrocardiography apparatus. After a digitization, the measured values are further-processed and the distribution of potential is displayed on an image playback device as a potential map, also referred to as Body Surface Potential Mapping (BSPM). The physician can then compare this potential map to a separately obtained potential map associated with the excitation anomaly in question. When the two potential maps are the same, it is assumed that the catheter is located at the location of the excitation anomaly. After such locating, a catheter ablation can be implemented for therapy. It is time-consuming to find and separate the ECG signals belonging to the stimulus from the continuously measured ECG signals. Further, the inherently continuous data acquisition must be stopped before the evaluation.

Page 163 of the book by Joseph Eichmeier, "Medizinische Elektronik," eine Einführung für Studierende der Ingenieurwissenschaften, Physik, Medizin und Biologie, Second Edition, Springer Verlag, Berlin Heidelberg, 1991, shows a block circuit diagram of an implanted defibrillator. Ventricular flutter or fibrillation is recognized therein by signal analysis of the ECG and analysis of the mechanical activity of the ventricle and an electric shock is triggered a few seconds later. The measured values of the ECG detector and of the mechanical detector are emitted uninterrupted to the further-processing unit, fashioned as a tachycardia recognition unit.

SUMMARY OF THE INVENTION

It is an object of the present invention to provide an apparatus wherein an allocation of the stimulation signal to the measured values causally influenced by the stimulated action current is simplified.

This object is achieved in an apparatus wherein means for supplying the measured values to the further-processing unit are connected to the stimulation unit and to the further-processing means dependent on the stimulation signals. The measured signals belonging to the stimulus can thus be identified and can then be interpreted with suitable methods.

DESCRIPTION OF THE DRAWINGS

The single FIGURE is a schematic illustration of an apparatus for acquiring stimulated action currents of the heart, constructed in accordance with the principles of the present invention.

DESCRIPTION OF THE PREFERRED EMBODIMENTS

A multi-channel electrocardiography system 6 has a number (such as thirty-two) of electrodes 4 that are arranged on the front side and back side of the torso of a patient 2 for measuring potentials on the body surface of the patient 2 produced by action currents in the heart. The multi-channel electrocardiography system 6, referred to below as ECG system 6, is of a conventional type and amplifies and (possibly) filters the measured values.

Further, a stimulation unit 8, which also includes a stimulation catheter 10, is required in order to stimulate action currents in the heart after being positioned therein. A suitable stimulation unit 8 is commercially obtainable from Siemens AG under the name "EPCOR".

The stimulation signal is triggered by means of a trigger signal emitted by a trigger generator 12 external to the stimulation unit 8, the trigger being supplied to the stimulation unit 8 via a potential-isolated lead 13.

Both the surface potentials produced by the natural action currents and the surface potentials that are evoked by the stimulation unit 8 are measured by the ECG system 6. The ECG system 6 is connected to control electronics 16 for data acquisition via a measured data line 14. The control electronics 16 supplies the analog measured data arriving parallel successively with a multiplexer 18 to a following analog-to-digital converter unit 20 that digitizes the measured values with the required precision. As a rule, a sampling rate of 1000 Hz per channel and a bit width of 16 bits are sufficient. As warranted, the multiplexer can be preceded by a sample and hold circuit.

At its output side, the control electronics 16 is connected via a data line 22 to a computer 24 that stores the digitized measured values and supplies them to a display 26 is a suitably edited form. For example, the model "SUN Sparc" can be employed as the computer 24, whereby the measured data are supplied via a parallel interface 28 according to the standard S11W.

An important feature in the inventive apparatus is that the digitization of the incoming analog measured signals does not ensue continuously, but only following a start signal supplied via an input 30. The start signal activates the clock output of an oscillator 32 with which the multiplexer and the analog-to-digital converter unit 20 are controlled. The start signal is emitted by the trigger generator 12 with a time allocation to the stimulation signal, being emitted on the basis of a corresponding operating action on the part of the physician or examining person. The actuation of an operating element symbolized by an arrow 34 generates a trigger signal, such as a pulse from a pulse source 36, from which the trigger for the stimulation unit 8 and the start signal for the control electronics 16 are derived. A time spacing from zero up to a maximum delay between the trigger and the start signal can be set via an adjustable delay 38, so that the start signal is possibly emitted by the outside trigger generator 12 chronologically preceding the trigger. The oscillator 32 is deactivated, i.e. stopped or inhibited, by a stop signal that the computer 24 emits via its parallel interface 28. The computer 24 generates the stop signal after a time duration that begins with the start signal. This time duration can be prescribed by the user for setting the length of the measured data interval.

The signal-to-noise ratio of the stimulated measured values can be improved when, given an unmodified catheter location, stimulation signals are repeatedly triggered and the potential values belonging thereto are subjected to an averaging procedure in the computer 24.

After the stimulation catheter has been introduced into the patient 2, ECG signals of a stimulated action current are first triggered, registered and stored. For example, the measured data interval lasts for one heart cycle. The computer 24 calculates a potential map from the stored signal of a prescribable point in time of a prescribable, characteristic signal curve such as, for example, a maximum amplitude within the measured data interval and supplies this potential map to the display 26. The physician can directly compare the potential map generated by the stimulus to the potential map of an anomalous action current. The ultimate positioning of the catheter 10 is then implemented under the supervision of further stimulation signals.

Although modifications and changes may be suggested by those skilled in the it is the intention of the inventors to embody within the patent warranted hereon all changes and modifications as reasonably and properly come within the scope of their contribution to the art.

We claim as our invention:

1. An apparatus for acquiring stimulated action currents of a heart of a patient, comprising:

stimulation means for emitting stimulation signals to said heart;

measuring means for acquiring measured values causally influenced by action currents in said patient resulting from said stimulation signals;

processing means for processing said measured values; and control means, connected to said stimulation means and to said processing means, for controlling delivery of said measured values to said processing means dependent on said stimulation signals by starting delivery of said measured values to said processing means at a same time as emission of said stimulation signals by said stimulations means.

2. An apparatus as claimed in claim 1 wherein said processing means comprise means for averaging said measured values.

3. An apparatus as claimed in claim 1 wherein said measurement means comprise means for acquiring said measured values in a measuring interval, and wherein said processing means include a picture screen display and means for producing a potential display on said picture screen display for each measuring interval dependent on a prescribable characteristic.

4. An apparatus as claimed in claim 1 wherein said measuring means comprise means for simultaneously acquiring a plurality of different measured values at different locations on said patient.

5. An apparatus as claimed in claim 1 wherein said measuring means comprise means for acquiring electrical potentials.

6. An apparatus as claimed in claim 5 wherein said measuring means comprise a plurality of body electrodes for acquiring said electrical potentials.

7. An apparatus for acquiring stimulated action currents of a heart of a patient comprising:

stimulation means for emitting stimulation signals to said heart;

measuring means for acquiring measured values causally influenced by action currents in said patient resulting from said stimulation signals;

processing means for processing said measured values; and control means, connected to said stimulation means and to said processing means, for controlling delivery of said measured values to said processing means dependent on said stimulation signals by starting delivery of said measured values to said processing means chronologically before emission of said stimulation signals by said stimulation means.

8. An apparatus as claimed in claim 7 wherein said processing means comprise means for averaging said measured values.

9. An apparatus as claimed in claim 7 wherein said measurement means comprise means for acquiring said measured values in a measuring interval, and wherein said processing means include a picture screen display and means for producing a potential display on said picture screen display for each measuring interval dependent on a prescribable characteristic.

10. An apparatus as claimed in claim 7 wherein said measuring means comprise means for simultaneously acquiring a plurality of different measured values at different locations on said patient.

11. An apparatus as claimed in claim 7 wherein said measuring means comprise means for acquiring electrical potentials.

12. An apparatus as claimed in claim 11 wherein said measuring means comprise a plurality of body electrodes for acquiring said electrical potentials.

13. An apparatus for acquiring stimulated action currents of a heart of a patient comprising:

stimulation means for emitting stimulation signals to said heart;

measuring means for acquiring measured values causally influenced by action currents in said patient resulting from said stimulation signals;

processing means for processing said measured values; and control means, connected to said stimulation means and to said processing means, for controlling delivery of said measured values to said processing means dependent on said stimulation signals by prescribing a time duration of delivery of said measured values to said processing means.

14. An apparatus as claimed in claim 13 wherein said processing means comprise means for averaging said measured values.

15. An apparatus as claimed in claim 13 wherein said measurement means comprise means for acquiring said measured values in a measuring interval, and wherein said processing means include a picture screen display and means for producing a potential display on said picture screen display for each measuring interval dependent on a prescribable characteristic.

16. An apparatus as claimed in claim 13 wherein said measuring means comprise means for simultaneously acquiring a plurality of different measured values at different locations on said patient.

17. An apparatus as claimed in claim 13 wherein said measuring means comprise means for acquiring electrical potentials.

18. An apparatus as claimed in claim 17 wherein said measuring means comprise a plurality of body electrodes for acquiring said electrical potentials.

* * * * *